United States Patent

Stache et al.

[11] 3,950,323
[45] Apr. 13, 1976

[54] DIGOXIGENINE-3-[2',3'-DIDESOXY-GLYCOSIDES] AND A PROCESS FOR THEIR MANUFACTURE

[75] Inventors: Ulrich Stache, Hofheim, Taunus; Werner Fritsch, Neuenhain, Taunus; Werner Haede, Hofheim, Taunus; Ernst Lindner, Frankfurt am Main, all of Germany

[73] Assignee: Hoechst Aktiengesellschaft, Frankfurt am Main, Germany

[22] Filed: Nov. 16, 1973

[21] Appl. No.: 416,656

[30] Foreign Application Priority Data
Nov. 20, 1972 Germany............................ 2256912

[52] U.S. Cl............................ 260/210.5; 424/182
[51] Int. Cl.²......................................... C07J 19/00
[58] Field of Search................................. 260/210.5

[56] References Cited
UNITED STATES PATENTS

| | | | |
|---|---|---|---|
| 3,642,770 | 2/1972 | Haede et al. | 260/210.5 |
| 3,838,146 | 9/1974 | Stache et al. | 260/210.5 |

FOREIGN PATENTS OR APPLICATIONS

| | | | |
|---|---|---|---|
| 1,943,901 | 5/1971 | Germany | 260/210.5 |

*Primary Examiner*—Lewis Gotts
*Assistant Examiner*—Cary Owens
*Attorney, Agent, or Firm*—Henry W. Koster

[57] ABSTRACT

Digoxigenine-3-[2', 3'-didesoxy-glycosides] of the formula

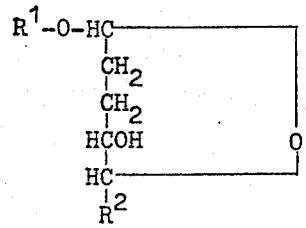

in which $R^1$ is the digoxigenine radical and $R^2$ is hydrogen, methyl or —$CH_2OH$, which are prepared by a reaction of a digoxigenine-12-monoacylate with an acylated 1,2-glycal, a catalytic hydrogenation of the 12-acylates obtained and a subsequent hydrolysis. The products have a cardiotonic, diuretic and especially venotonic activity.

1 Claim, No Drawings

DIGOXIGENINE-3-[2′,3′-DIDESOXY-GLYCOSIDES] AND A PROCESS FOR THEIR MANUFACTURE

The present invention relates to digoxigenine -3-[2′, 3′-didesoxy-glycosides] and to a process for the manufacture thereof.

According to German Offenlegungsschrift No. 1,943,901, it is known to prepare -3-[2′, 3′-didesoxy-glycosides ] by reacting cardenolide aglucones with acyl glycals, catalytically hydrogenating the reaction products selectively in 2′ (3′)-position and then hydrolyzing the acyl groups. When, as a cardenolide aglucone, digoxigenine containing, in addition to a hydroxy group in 3-position, another hydroxy group in 12β-position, is reacted with an acyl glycal, this acyl glycal is not selectively added on the 3-hydroxy group only but also - and this is undesirable - on the 12β-hydroxy group. So, when digoxigenine-3-[2′, 3′-didesoxy-glycosides] are to be prepared, the 12β-hydroxy grooup has to be protected selectively.

This invention now provides digoxigenine-3-[2′, 3′-didesoxy-glycosides] of the formula I

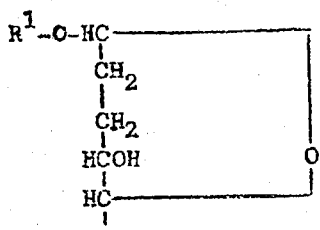

in which $R^1$ stands for the digoxigenine radical and $R^2$ for hydrogen, methyl or the group —$CH_2OH$.

This invention also provides a process for the manufacture of digoxigenine-3-[2′, 3′-didesoxy-glycosides] of the formula I as specified above, which comprises reacting a digoxigenine-12-monoacylate of the formula II

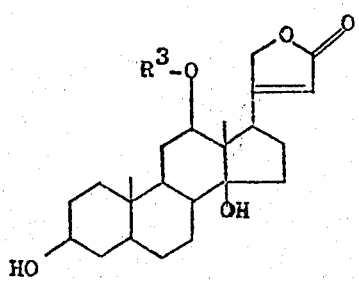

in which $R^3$ stands for an acyl radical of 1 to 4 carbon atoms, with an acylated 1,2-glycal of the formula III

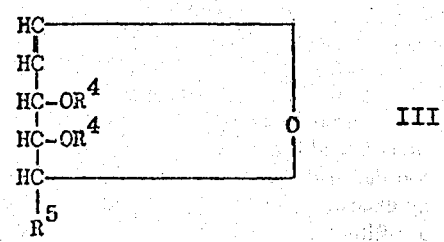

in which $R^4$ stands for an aliphatic acyl radical of 1 to 4 carbon atoms, a cycloaliphatic acyl radical of 6 or 7 carbon atoms, a phenyl-acetyl group, a benzoyl group or an ortho-, para- or meta-nitrobenzoyl group, and $R^5$ stands for hydrogen, methyl or the group —$CH_2OR^4$, in the presence of an acid catalyst, catalytically hydrogenating the so-obtained digoxigenine-3-[2′, 3′-didesoxy-$\Delta^{2'\,(3')}$-glycoside]-12-acylate of the formula IV

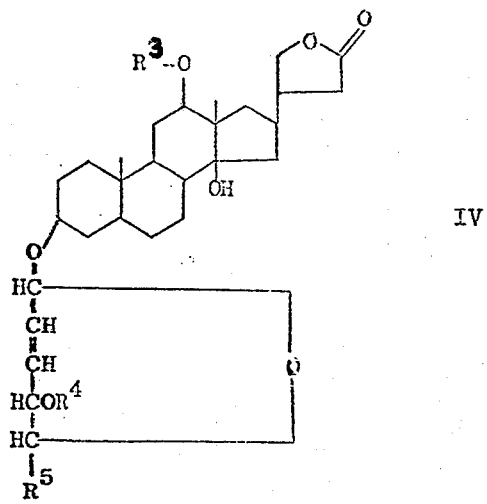

in which $R^3$, $R^4$ and $R^5$ are defined as above, in 2′ (3′)-position in the presence of a metal catalyst in an inert solvent and then hydrolyzing the compound thus obtained.

As digoxigenine-12-monoacylate of the formula II is, for example, mentioned digoxigenine-12-monoacetate to be prepared according to Helv. Chim. Acta, 39, 1712 (1956), preferably digoxigenine-12-monoformiate which can easily be saponified by alkaline agents and may be obtained by reacting digoxigenine with a mixed anhydride of formic acid and acetic acid in pyridine at 0°C and pouring the reaction mixture into water, then extracting it with methylene chloride and, where required, finally purifying it by chromatography (melting point: 258°–260°C).

The acylated 1,2-glycals of the formula III may be prepared according to Ber. Dtsch. chem. Ges. 47, 196 (1914). Exemplary thereof are acylated arabinals, xylals, glucals, galactals, allomethylals or rhamnals, the acyl radicals $R^4$ being especially formyl, acetyl or propionyl, as well as benzoyl or nitrobenzoyl.

Solvents to be used for the first reaction step are ethers, such as diethyl ether, tetrahydrofuran, dioxan or other solvents which do not react with the glycals, such as dimethylformamide or acetone.

The reaction is carried out at a temperature of from 0°C to the boiling temperature of the solution used, preferably at room temperature. The reaction times are in the range of from a few minutes to several hours.

As acid catalysts, concentrated mineral acids, sulfonic acids or phosphoroxy chloride are used.

The products of the first reaction step according to the invention are advantageously isolated by neutralizing and concentrating the reaction solution and then precipitating the reaction product with water. After neutralization, however, the product may also be extracted with an organic solvent and, after concentration, it may be crystallized or, after the extracting agent has been distilled off, it may be crystallized from another suitable solvent.

The selective catalytic hydrogenation of the 2(3)-double bond in the glycoside moiety may be performed using, as catalysts, for example palladium, platinum, rhodium, zinc, nickel or iridium catalysts or mixtures of these catalysts, preferably palladium catalysts, such as palladium supported on activated carbon or on barium- or strontium carbonate.

Solvents used for the catalytic hydrogenation are, for example, methylene chloride, chloroform, dichloroethane, tetrahydrofuran, dioxan, methanol, ethanol, propanol, benzene, toluene or mixtures of these solvents.

Catalytic hydrogenation is performed using hydrogen at atmospheric pressure or at pressures of up to about 50 atmospheres gage and at a temperature of from 0° to 70°C, preferably from 20° to 50° C, in an apparatus suitable for such a reaction. It is important that, after 1 molar equivalent of hydrogen has been absorbed, the catalytic hydrogenation is discontinued unless it comes to a standstill anyway after absorption of this hydrogen amount. By checking the UV-absorption on a sample of the reaction mixture in the range of from 207 to 220 mμ, corresponding to the absorption of the 17β-butenolide ring, one can make sure of how the hydrogenation reaction proceeds. There must not be a catalytic hydrogenation of the butenolide double bond, which would be recognized by a decrease in the extinction of the above-said UV-absorption. After the double bond in the glycoside moiety has been hydrogenated completely, the catalyst is separated from the solution by suction-filtration, the filtrate is concentrated and the residue is recrystallized from a suitable solvent or mixture of solvents. It is sometimes advantageous to carry out a previous separation by chromatography.

When digoxigenine-12-monoformiate is used as starting material, the alkaline hydrolysis of the hydrogenated compound yielding digoxigenine-3-[2', 3'-didesoxy-glycosides] may be carried out under gentle conditions. Thus, for example, both the 12-formiate group in the aglucone moiety and the acyl group in the glycoside moiety are completely saponified by a hydrolysis with potassium hydrogenocarbonate in a mixture of alcohol and water at boiling temperature over 30 minutes, without adversely affecting the characteristic structure which is relevant to a cardiotonic efficacy, such as the 14β-hydroxy group and the 17β-butenolide ring. Moreover, hydrolysis may also be brought about according to one of the conventional methods, for example using ammonia in methanol or ethanol.

When a digoxigenine-12-monoacylate having a different acyl group in 12-position, for example digoxigenine-12-monoacetate, is used as starting material, hydrolysis of the 12-acetate group cannot be brought about under the conditions indicated for the 12-formiate group. Only the acylate groups in the glycoside moiety are hydrolyzed. The 12-acetate group is neither saponified to an appreciable extent by heating the material for more than 30 minutes with potassium hydrogenocarbonate in alcohol/water nor by allowing it to stand for more than 48 hours in ammonia/methanol. However, the structural features relevant to cardiotonic efficacy are chemically modified to an undesirable extent under those conditions.

A complete hydrolysis of the 12-acetate group in addition to the acyl groups in the glycoside moiety is, however, possible under the following special hydrolysis conditions: For hydrolyzing digoxigenine-12-monoacetate-3-[2', 3'-didesoxy-acyl-glycosides] to yield digoxigenine-3-[2', 3'-didesoxy-glycosides], it is advantageous first to hydrolyze the acyl groups in the glycoside moiety by heating it for 30 minutes at the boil with potassium hydrogenocarbonate in alcohol/water. After the usual work-up, for example by pouring the hydrolysis mixture into water saturated with sodium chloride and isolating the precipitate thus obtained, this precipitate is treated twice successively with potassium hydrogenocarbonate and methanol/water, as disclosed in Example 6, for 4 to 5 weeks at 15°–25°C and then worked up in the usual manner. In the thin-layer chromatogram, the reaction product thus obtained does no longer show an appreciable amount of 12-acetate derivatives of digoxigenine-3-[2', 3'-didesoxyglycoside]. Recrystallization, preferably effected from isopropanol/diisopropyl ether, entirely eliminates any trace of digoxigenine-glycosides still acetylated in 12-position as well as further by-products, if any. In this manner, uniform digoxigenine-3-[2', 3'-didesoxyglycosides] are obtained, as thinlayer chromatography shows.

The digoxigenine-3-[2', 3'-didesoxy-glycosides] according to the invention have valuable pharmacological properties. For example, they show cardiotonic efficacy, especially a positively inotropic effect, as well as diuretic, antidiarrheal and, in particular venotonic properties. It is especially worth mentioning that the compounds according to the invention are well absorbed upon enteral administration and that their effect wears off relatively quickly, thus assuring an easy control and a raapid degradation of the compounds in the metabolism during the treatment of heart diseases.

For example, digoxigenine-3-L-[2', 3'-didesoxyrhamnoside] (see Example 3) shows a substantially stronger effect in the potassium excretion test on an isolated heart of a guinea pig than digoxine does.

The compounds according to the invention may be administered per os in the form of dragees, tablets or gelatine capsules, in admixture with the usual excipients, such as starch, lactose, cellulose powder, finely divided silicic acid, where required with a constituent, such as cane sugar, talcum or magnesium stearate. Moreover, aqueous alcoholic solutions may also be used for liquid medicinal units.

For a parenteral administration, aqueous-alcoholic solution, where required in admixture with glycols, such as propylene glycol, may be used, after having been sterilized, for example, by sterile filtration.

The following Examples illustrate the invention.

EXAMPLE 1

Digoxigenine-3-L-[2', 3'-didesoxy-4'-O-acetyl-$\Delta^{2'(3')}$-rhamnoside]-12-formiate 7 Ml of diacetyl-L-rhamnal and 0.3 Ml of phosphoroxy chloride were added to a solution of 4.1 g of digoxigenine-12-monoformiate in 38 ml of absolute tetrahydrofuran. After having been stirred for 5 hours at 20°–25°C (while care was taken that the reaction mixture was not heated above 40°C, since otherwise undesirable by-product that are difficult to be separated would form, thus decreasing the yields), the reaction mixture was poured into 300 ml of water containing excess $NaHCO_3$, the precipitate obtained was suction-filtered, washed with water, dissolved in methylene chloride, washed again with water, dried and concentrated under reduced pressure. The oil obtained (about 8 g) was crystallized from ether. 4.9 g of digoxigenine-3-L-[2', 3'-didesoxy-4'-O-acetyl-$\Delta^{2'}$ ⁽³'⁾-rhamnoside]-12-formiate were obtained, melting point about 285°C. This compound was used for the following reaction without subsequent treatment.

Characteristic infrared bands (in KBr): 3560, 3480, 3420 and 3400 3400(shoulders), 1780, 1750, 1740–1710 (several bands), 1615, 1235, 1180, 1150, 1025, 1000, 730 cm$^{-1}$.

In the same manner as disclosed above, digoxigenine-12-monoformiate was reacted with diacetyl-D-rhamnal to yield digoxigenine-3-D-[2', 3'-didesoxy-4'-O-acetyl-$\Delta^{2'}$ ⁽³'⁾-rhamnoside]-12-formiate, or it was reacted with diacetyl-D-xylal to yield digoxigenine-3-D-[2', 3'-didesoxy-4'-O-acetyl-$\Delta^{2'}$ ⁽³'⁾-xylopyranoside]-12-formiate, or it was reacted with diacetyl-L-xylal to yield digoxigenine-3-L-[2', 3'-didesoxy-4'-O-acetyl-$\Delta^{2}$ ⁽³⁾-xylopyranoside]-12-formiate.

EXAMPLE 2

Digoxigenine-3-L-[2', 3'-didesoxy-4'-O-acetyl-rhamnoside]-12-formiate

A solution of 3.7 g of digoxigenine-3-L-[2', 3'-didesoxy-4'-O-acetyl-$\Delta^{2'}$ ⁽³'⁾-rhamnoside]-12-formiate in 100 ml of tetrahydrofuran was added to a pre-hydrogenated suspension of 1.5 g of palladium on calcium carbonatte (of 10% strength) in 50 ml of ethanol and the mixture was hydrogenated at 22°C under atmospheric pressure. After 1 molar equivalent of hydrogen (= 155 ml) had been absorbed, hydrogenation came to a standstill. The catalyst was separated from the solution by filtration and the filtrate was concentrated under reduced pressure. The oil obtained as a residue was crystallized from diisopropyl ether.

3.3 G of digoxigenine-3-L-[2', 3'-didesoxy-4'-O-acetyl-rhamnoside]-12-formiate were obtained, m.p. 225°C.

Characteristic infrared bands (in KBr): 3470, 1775, 1750, 1735-1710, 1615, 1240, 1185, 1015, 1000 cm$^{-1}$.

In the same manner as disclosed above, digoxigenine-3-D-[2', 3'-didesoxy-4'-O-acetyl-rhamnoside]-12-formiate was obtained from digoxigenine-3-D-[2', 3'-didesoxy-4'-O-acetyl-$\Delta^{2'}$ ⁽³'⁾-rhamnoside]-12-formiate and digoxigenine-3-D- (or L-) [2', 3'-didesoxy-4'-O-acetyl-xylopyranoside]-12-formiate from digoxigenine-3-D- (or L-)-[2', 3'-didesoxy-4'-O-acetyl-$\Delta^{2'}$ ⁽³'⁾-xylopyranoside]-12-formiate.

EXAMPLE 3

Digoxigenine-3-L-[2', 3'-didesoxy-rhamnoside]

To saponify the 4'-acetate and 12-formiate groups, 1.2 g of digoxigenine-3-L-[2', 3'-didesoxy-4'-O-acetyl-rhamnoside]-12-formiate were dissolved or suspended in 38 ml of methanol, and a solution of 720 mg of potassium bicarbonate in 3.8 ml of water was added thereto at the boil. The reaction mixture was refluxed for 30 minutes, then cooled to 20°C and poured onto 200 ml of a semisaturated aqueous sodium chloride solution, whereupon crystals precipitated. They were extracted with methylene chloride, washed with water, dried and concentrated under reduced pressure. The residue was crystallized from diisopropyl ether and yielded 877 mg of crude digoxigenine-3-L-[2', 3'-didesoxy-rhamnoside], which were recrystallized from a mixture of isopropanol and diisopropyl ether. M.p. 244°C.

Characteristic infrared bands (in KBr): 3450, 1770, 1730, 1625, 1105, 1020, 980, 945, 850 cm$^{-1}$. UV spectrum: $\lambda$ max = 217–218 m$\mu$, $\epsilon$ = 16400 (CH$_3$OH)

In the same manner as disclosed above, digoxigenine-3-D-[2', 3'-didesoxy-rhamnoside] could be prepared form digoxigenine-3-D-[2', 3'-didesoxy-4'-O-acetyl-rhamnoside]-12-formiate and digoxigenine-3-D- (or L) - [2', 3'-didesoxy-xylopyranoside] from digoxigenine-3-D- (or L) - [2', 3'-didesoxy-4'-O-acetyl-xylopyranoside]-12-formiate.

EXAMPLE 4

Digoxigenine-3-L-[2', 3'-didesoxy-4'-O-acetyl-$\Delta^{2'}$ ⁽³'⁾-rhamnoside]-12-acetate 18 Ml of diacetyl-L-rhamnal and 0.8 ml of phosphoroxy chloride were added to a suspension of 12 g of digoxigenine-12-monoacetate in 100 ml of absolute tetrahydrofuran. After having been stirred for 7 hours at 20°–25°C, the reaction mixture was poured onto 2 l of water containing excess NaHCO$_3$, extracted with methylene chloride, washed with water, dried and concentrated under reduced pressure. An oil was obtained which was crystallized form ether to yield 6.5 g of crystal material (crystal fraction). The mother liquor was chromatographed on 220 g of aluminium oxide (Woelm, neutral, activity stage II), successively with 500 ml of benzene (first fraction), 1 l of benzene/methylene chloride (2 : 1) (second fraction) and 2 l of benzene/methylene chloride (1 : 1) (third fraction). After the third fraction had been concentrated, 4.5 g of crystal material were obtained upon further crystallization from ether. All the physical data of this last fraction corresponding to those of the first crystal fraction obtained. The overall yield of digoxigenine-3-L-[2', 3'-didesoxy-4'-O-acetyl-$\Delta^{2'}$ ⁽³'⁾-rhamnoside]-12-acetate was 11 grams and the melting point was 199°C.

Characteristic infrared bands (in KBr): 3500, 1780, 1750, 1730, 1625, 1235, 1025, 990, 740 cm$^{-1}$.

EXAMPLE 5

Digoxigenine-3-L-[2', 3'-didesoxy-4'-O-acetyl-rhamnoside]-12-acetate

A solution of 8 g of digoxigenine-3-L-[2', 3'-didesoxy-4'-O-acetyl-$\Delta^{2'}$ ⁽³'⁾-rhamnoside]-12-acetate in 100 ml of ethanol was added to a pre-hydrogenated suspension of 1.2 g of palladium on calcium carbonate (of 10% strength) in 40 ml of ethanol, and the mixture was hydrogenated at 22°C under atmospheric pressure. After 1 molar equivalent of hydrogen had been absorbed, hydrogenation came to a standstill. The catalyst was separated by filtration and the filtrate was concentrated under reduced pressure. The oil obtained as a residue was crystallized from diisopropyl ether.

7.4 G of digoxigenine-3-L-[2', 3'-didesoxy-4'-O-acetyl-rhamnoside]-12-acetate were obtained, m.p. 215°C.

Characteristic infrared bands (in KBr): 3500, 1780, 1750, 1730, 1710, 1625, 1240, 1025, 995 cm$^{-1}$.

EXAMPLE 6

Digoxigenine-3-L-[2', 3'-didesoxy-rhamnoside]

2.5 G of digoxigenine-3-L-[2', 3'-didesoxy-4'-O-acetyl-rhamnoside]-12-acetate were dissolved or suspended in 75 ml of methanol and a solution of 1.35 g of potassium bicarbonate in 10 ml of water was added thereto at boiling temperature. The reaction mixture was refluxed for 30 minutes, then cooled and poured into 400 ml of semisaturated aqueous sodium chloride solution. The crystals thus obtained were suction-filtered (2 g of dry weight; infrared spectrum still showed acetate bands at about 1240 cm$^{-1}$). The crystals were dissolved in 55 ml of methanol and allowed to stand with a solution of 400 mg of potassium bicarbonate in 5.9 ml of water for 28 days at 20°–22°C. The solution was then poured into water, extracted with chloroform, washed with water, dried and concentrated under reduced pressure. The foamy substance obtained (1.6 g) still showed a pronounced acetate band in the infrared spectrum at 1240 cm$^{-1}$. The substance was once more dissolved in 130 ml of methanol and a solution of 1.33 g of potassium bicarbonate in 41 ml of water was added. After the mixture had stood for another 28 days at 20°–22°C, methanol was distilled off, the residue was extracted with methylene chloride, washed with water, dried and concentrated under reduced pressure.

880 Ml of crude digoxigenine-3-L-[2', 3'-didesoxy-rhamnoside] were obtained which were first recrystallized from methanol/ether and then from isopropanol/diisopropyl ether. The product thus obtained showed the same physical data as that obtained according to Example 3.

The thin-layer chromatogram showed only one spot having an $R_f$-value of about 0.27 without secondary spots (benzene:methanol:acetone = 8:2:0.5; colored with ethanol/p-toluene-sulfonic acid; developed once).

What we claim is:
1. Digoxigenine-3-L-[2', 3'-didesoxy-rhamnoside].

* * * * *